United States Patent [19]

Lai

[11] Patent Number: 5,876,444
[45] Date of Patent: Mar. 2, 1999

[54] RECONSTITUTED COLLAGEN TEMPLATE AND THE PROCESS TO PREPARE THE SAME

[76] Inventor: Wen-fu Lai, No. 23, Alley 6, Lane 118, Sec. 2, Hoping E. Rd., Taipei, Taiwan

[21] Appl. No.: 626,635

[22] Filed: Apr. 1, 1996

[51] Int. Cl.$^6$ .......................................................... A61F 2/02
[52] U.S. Cl. ............................................ 623/11; 424/423
[58] Field of Search ...................... 623/11; 424/422–426

[56] References Cited

U.S. PATENT DOCUMENTS

| | | | |
|---|---|---|---|
| 4,185,011 | 1/1980 | Eckmayer et al. .................... | 260/123.7 |
| 4,233,360 | 11/1980 | Luck et al. ............................... | 428/310 |
| 4,597,762 | 7/1986 | Walter et al. ............................... | 623/1 |
| 5,411,887 | 5/1995 | Sjdlander .................................. | 435/273 |

OTHER PUBLICATIONS

J.D. Bruijn et al., "Failure of the Mecring Screw–Ring Acetabular Component in Total Hip Arthroplasty", J. Bone and Joint Surg., 77(5): 760–766 (1994).

H.C. Grillo, et al., "Thermal Reconstitution of Collagen from Solution and the Response to Its Heterologous Implantation", J. Surg. Res., 2, 69 (1962).

J.I. Abbenhaus et al., "Collagen Sheets as a Dressing for Large Excised Areas", Surg. Forum, 16, 477 (1965).

J.B. Yannas et al., "Viscoelastic Properties of Plasticized Gelatin Films", J. Phy. Chem., 68, 3880 (1964).

J. Einbinder et al., "Binding of Mucopolysaccharides and Dyes by Collagen", J. Biol. Chem., 188, 335 (1951).

*Primary Examiner*—John G. Weiss
*Assistant Examiner*—John M. Black
*Attorney, Agent, or Firm*—Hedman, Gibson & Costigan, P.C.

[57] ABSTRACT

The present invention relates to a process of preparation of a new reconstituted collagen template and further to the reconstituted collagen template being able to cure articular destruction in a mammal.

6 Claims, 12 Drawing Sheets

RECONSTITUTED COLLAGEN TEMPLATE AND THE PROCESS TO PREPARE THE SAME

BACKGROUND OF THE INVENTION

The present invention relates to a new reconstituted collagen template and a process of the preparation thereof. The present invention also relates to use of the new reconstituted collagen template for activating regeneration of the articular tissues and thereby curing articular destruction.

Arthropathy is one of the persistent diseases found in throughout the history of mankind. Among other articular diseases, the major types of human non-congenital arthropathy are etiologically attributed to inflammatory/degenerative conditions. Generally the types of the inflammatory articulation diseases, i.e., arthritis, are characterized in the ongoing of the articular inflammation due to the long-term and/or intolerant mechanical stresses, and/or the attack of the immune system. The former condition, e.g., the degenerative arthritis, will always lead to the destruction of the articular cartilage or the meniscus disc and the latter condition, e.g., the rheumatoid arthritis, will lead to the invasive growth of the pannus, which is formed by the continuous proliferation of the synovial cells in cases of the immunosuppression, into zones of articular chondrocytes. The severe damage of the articulation has been found in each of the above conditions.

The articular chondrocytes are embraced and offered by the extracellular matrix. Once the metabolic support for the chondrocytes from the extracellular matrix has become deficient or absent due to the physical or physiological damages of the articulation, the chondrocytes die rapidly in an extent, i.e., atrophy of the articular cartilage, and the infiltration of lymphocytes is observed in the articular tissues. As used herein, the term "articular tissues" means the tissues including articular disc, cartilage and synovial lining. Furthermore, the fibroblasts are then activated to cause the fibrosis of the articulation if the chondrocytes cannot be activated to proliferate so as to reconstitute the cartilage in a period. This will cause irreversible destruction, followed by the dysfunction of the stressed articulation.

Since the irreversible destruction of the articular tissues and the failure to regenerate the chondrocytes are commonly observed in clinics, the attempts to replace the dysfunctional articulation with the artificial metal articulation have been performed in recent years. Although a metal articulation may actually substitute for part of the functions of a natural articulation; however, it is believed that the metal articulation may result in some unavoidably deleterious effects, e.g., the subsequent occurrence of the alkylosis, the unstable conjugation of the metal articulation by mechanical stresses as investigated by, e.g., Bruijn et. al. J. Bone and Joint Surg. 77(5): 760–766 (1994), or the synovitis as a result of the polymers, e.g., silicon gel adhered to the metal surfaces of artificial epiphyses. Therefore, a metal articulation sufficient to fully substitute for a destroyed natural articulation has not been developed in the art.

Therefore, there is still a need to find a therapeutic strategy for curing the arthropathy.

Nature collagen is one of the major types of proteins in a mammal and has been employed in preparing artificial skin, drug delivery, cosmetics, nutrients supply and so on. Grillo et. al. [J. Surg. Res., 2, 69 (1962)] showed that the cross-linking of the collagen by formaldehyde may decrease the rate of biodegradation. Abbenhaus et. al., Surg. Foru. 16, 477 (1965) disclosed the use of the collagen as the temporary material posed on a relatively large area of the wound. Yannas et. al. J. Phy. Chem., 68, 3880 (1964) disclosed that the gelatin rubber is able to undergo mechanical stresses. However, due to the distinct types and contents among varied tissues, collagen has not been successfully applied to the repair of the articulation.

The objective of the present invention is to provide a new reconstituted collagen template for use in facilitating the regeneration of the chondrocytes and the extracellular matrix of a stressed articulation and curing the articular destruction. The implantation of the reconstituted collagen template according to the present invention is effective in preventing the irreversible destruction of the articulation and the inconvenience of a metal articulation.

SUMMARY OF THE INVENTION

The present invention provides a new reconstituted collagen template which is derived from natural collagen, especially collagen type I.

It is surprisingly found that the implantation of the reconstituted collagen template according to the present invention to articular wounds is very effective in facilitating regeneration of the chondrocytes and extracellular matrix of a stressed articulation and curing of articular destruction.

In a further aspect of this invention, the process to prepare the reconstituted collagen template according to the present invention is provided, comprising the uncoiling of the triple-helix structure of natural collagen to α-helix monomers by using a proteolytic enzyme, such as pepsin and the cross-linking of these monomers by utilizing glutaraldehyde to a template with a regular pore size.

BRIEF DESCRIPTION OF THE DRAWINGS

FIGS. 7 (a) and (b) are photomicroscopic photographs (12× and 48× respectively) of the coronal tissue section of the TMJ disc of the New Zealand rabbit undergoing a partial diskectomy on a posterio-lateral portion for three months;

FIGS. 8 (a) and (b) are photomicroscopic photographs (12× and 48× respectively) of the coronal tissue section of the TMJ disc of the New Zealand rabbit undergoing a partial diskectomy on the posterio-lateral portion and the implantation of the reconstituted collagen template according to the present invention for three months;

FIGS. 9 (a) and (b) are photomicroscopic photographs (12× and 48× respectively) of the coronal tissue section of the TMJ disc of the New Zealand rabbit undergoing a partial diskectomy on the posterio-lateral portion and the implantation of the reconstituted collagen template according to the present invention for one month;

FIGS. 10 (a) and (b) are photomicroscopic photographs (48× and 480× respectively) of the coronal tissue section of the TMJ disc of the New Zealand rabbit undergoing a partial diskectomy on the posterio-lateral portion and the implantation of the reconstituted collagen template according to the present invention for one month;

FIGS. 11 (a) and (b) are photomicroscopic photographs (12× and 120× respectively) of the coronal tissue section of the TMJ disc of the New Zealand rabbit undergoing a partial diskectomy on the posterio-lateral portion and the implantation of the reconstituted collagen template according to the present invention for a week.

DETAILED DESCRIPTION OF THE PREFERRED EMBODIMENTS

The present invention provides a process to prepare a reconstituted collagen template according to the present invention, which comprises uncoiling a triple-helical collagen (type I) with a proteolytic cleavage of telopeptides to obtain α-helical monomers, reducing residue disulfide bonds in collagen to be the —SH groups by utilizing mercaptoethanol, and cross-linking the α-helical monomers by utilizing glutaraldehyde. Resultant products are lyophilized to obtain the reconstituted collagen template according to the present invention, which is in a net form with regular pores.

Glutaraldehyde is able to react with amino groups of the amino acids such as asparagine, arginine and glutamine in collagen to form a glutaraldehyde-polymer amine complex, as shown below.

According to the present invention the ratios of pepsin to the protein substrate thereof are usually from about 1:10 to about 1:5 (unit/mg protein substrate), and preferably from about 1:10 to about 1:8. The preferred concentrations of mercaptoethanol according to the present invention are from about 1.8% to about 2.0% (v/v).

In the embodiment of the present invention, utilizations of varied concentrations (0.5 to 25% (v/v)) and different reaction times (one to eleven days) of glutaraldehyde in cross-linking of the reconstituted collagen have obtained the reconstituted collagen template with a pore size 30 to 150 microns in diameter.

In the embodiment of the invention, the reconstituted collagen template according to the present invention is implanted in articular wounds. It is surprisingly found that the net form of the reconstituted collagen template according to the present invention could induce immigration of the articular fibrous chondrocytes and the synovial cells and subsequently incidence of fibrosis or ossification decreases. Therefore it is beneficial to activate the regeneration of the meniscus disc and the fibrous cartilage.

It is also surprisingly found that the implantation of the reconstituted collagen template according to the present invention could not only result in a cushion effect to the stressed articulation but also act as the intracellular matrix to offer the articular chondrocytes and the synovial cells.

It is also surprisingly found that the reconstituted collagen template according to the present invention is able to resist bio-degradation in vivo for a period sufficient to support regeneration of the articular tissues.

It is also surprisingly found that the regular pore size of the reconstituted collagen template according to the present invention could form a barrier against monocytes and prevent the formation of granulation tissues. Invasiveness of arthritis is thus alleviated or arrested.

It is also surprisingly found that an immunoresponse in implantation recipients of the reconstituted collagen template according to the present invention was reduced to allow the regeneration of the articular tissues as a result that the α-helical feature is retained in the reconstituted collagen template.

Type I collagen (purchased from Sigma (C 9819), purified according to Einbinder et. al., J. Biol. Chem., 188, 335 (1951)) was added to deionic water in a final concentration of 10 mg/ml and heated to from about 55° C. to about 65° C. 3M HCl was then added to adjust a pH level to be about 1.8 to about 2.2. The acidic solution was centrifuged at 4° C. in 10,000–15,000 rev/min. The pellet was obtained by discarding the supernatant, taken into the deionic water and then pepsin (1:10 unit/mg protein substrate) was added, as shown in Reaction Scheme I.

Reaction Scheme I

A resultant solution of Reaction Scheme I was adjusted to a level of pH 10 by adding 5M NaOH and then reduced by adding mercaptoethanol, as shown in Reaction Scheme II.

Reaction Scheme II

Further details of this invention are demonstrated in the following examples.

EXAMPLES

1. The Preparation of the Reconstituted Collagen Template

The resultant α-helical monomers from Reaction Scheme II was cross-linked by utilizing glutaraldehyde in three concentrations (0.5, 2.5 and 25%) for 24 hours to 11 days and the desired glutaraldehyde-polymer amine complex was obtained, as shown in Reaction Scheme III.

Reaction Scheme III

The resultant reconstituted collagen solution from Reaction Scheme III was adjusted to a pH level of 7. The solution was diluted by deionic water (1:50) and then centrifuged (rpm 10,000) for 30 minutes. This step was repeated for 8 to 10 times to remove glutaraldehyde. A resultant solution was poured into molds and stored at −70° C. for about 8 hours before it was lyophilized for 18 to 24 hours.

2. The Electromicroscopic Examinations of the Reconstituted Collagen Templates 2.1. Materials and the Method Specimens (1×1×0.5 mm) taken from the reconstituted collagen templates prepared according to the above procedure were immediately fixed for 2.5 to 3 hours at 20° C. in 2% glutaraldehyde containing 0.7% (w/v) ruthenium hexamine trichloride (RHT) and 0.5 mol/L sodium cacodylate buffer, pH 7.4, 330±20 mOsm. The specimens were washed three times each for 15 min. in the buffer (pH 7.4, 330±20 mOsm). The specimens were then post-fixed for 2.5 to 3 hours at 20° C. in 1% (w/v) osmium tetroxide containing 0.7% (w/v) RHT and 0.1 mol/L sodium cacodylate buffer, pH 7.4, 330±20 mOsm.

After post-fixation, the specimens were dehydrated in ethanol with gradient concentrations (70 to 100%) and then coated with gold. The specimens were placed in isoamyl acetate and followed by critical point drying. The specimens were examined with a light microscope (OLYMPUS BH-2) and photographed (OLYMPUS C-35AD-4) to check adequacy of chondrocyte fixation so as to select an area of interaction for further electron microscope observation. Appropriate specimens were examined and photographed with Hitachi S2700 Scanning Electron Microscope at 10 kV.

2.2. Results:

2.2.1. Electromicroscopic Observations

Figure 1:
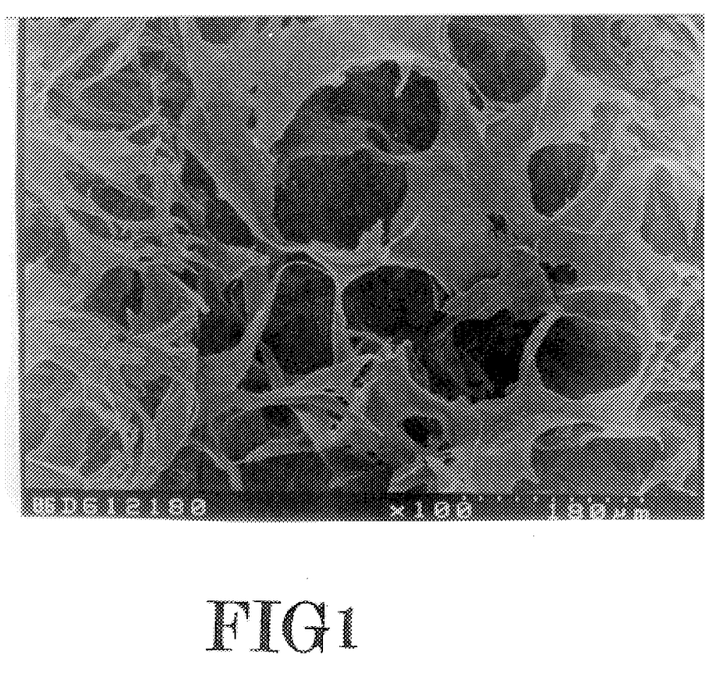
FIG. 1 is an electromicroscopic photograph (360×) of a reconstituted collagen template cross-linked by utilizing 0.5% glutaraldehyde.
Figure 2:
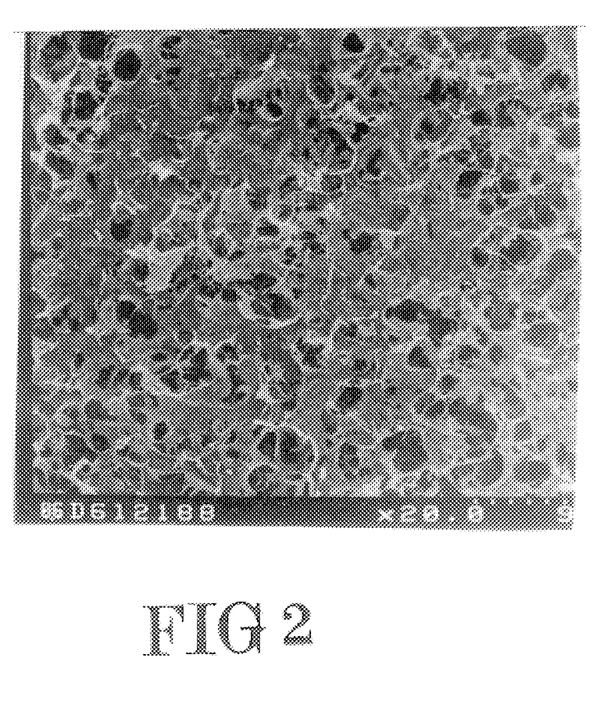
FIG. 2 is an electromicroscopic photograph (72×) of the reconstituted collagen template cross-linked by utilizing 2.5% glutaraldehyde.
Figure 3:
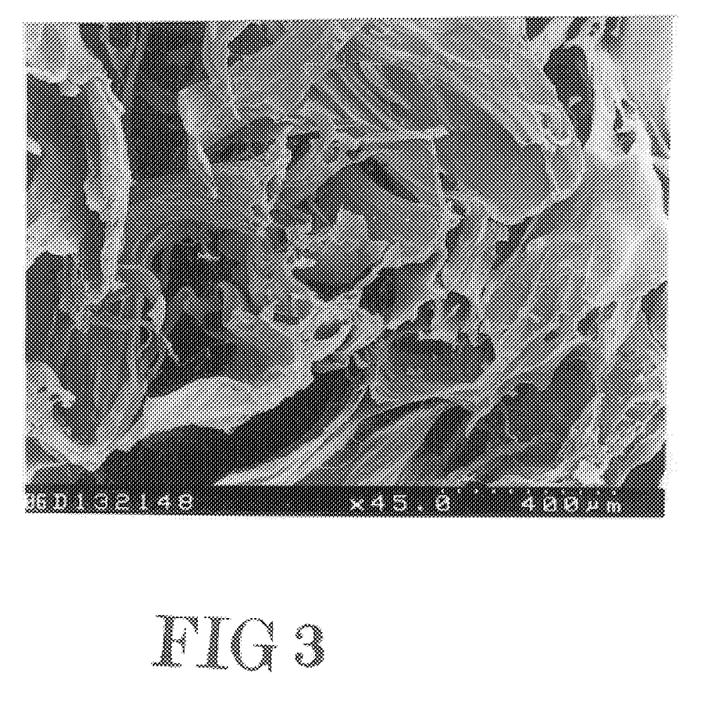
FIG. 3 is an electromicroscopic photograph (162×) of the reconstituted collagen template cross-linked by utilizing 25% glutaraldehyde.
Figure 4:
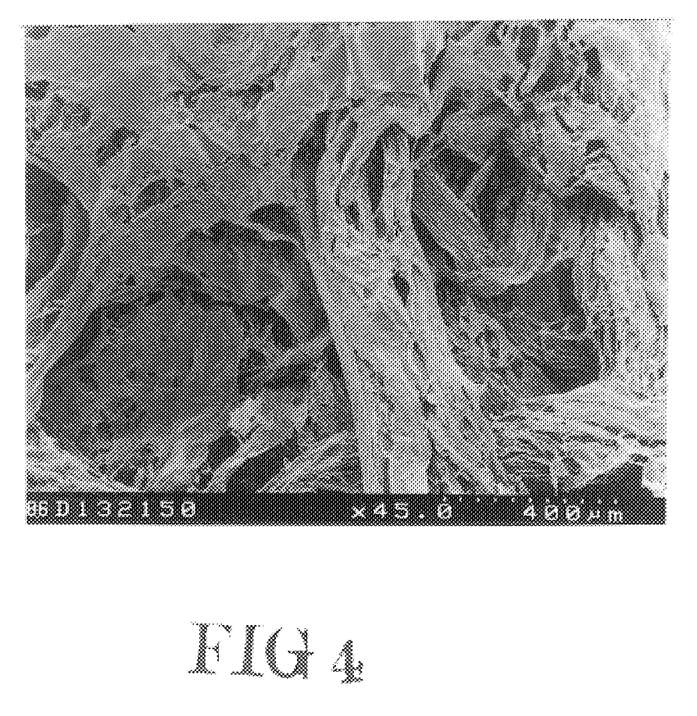
FIG. 4 is an electromicroscopic photograph (360×) of the reconstituted collagen template cross-linked by lyophilization.
Figure 5:
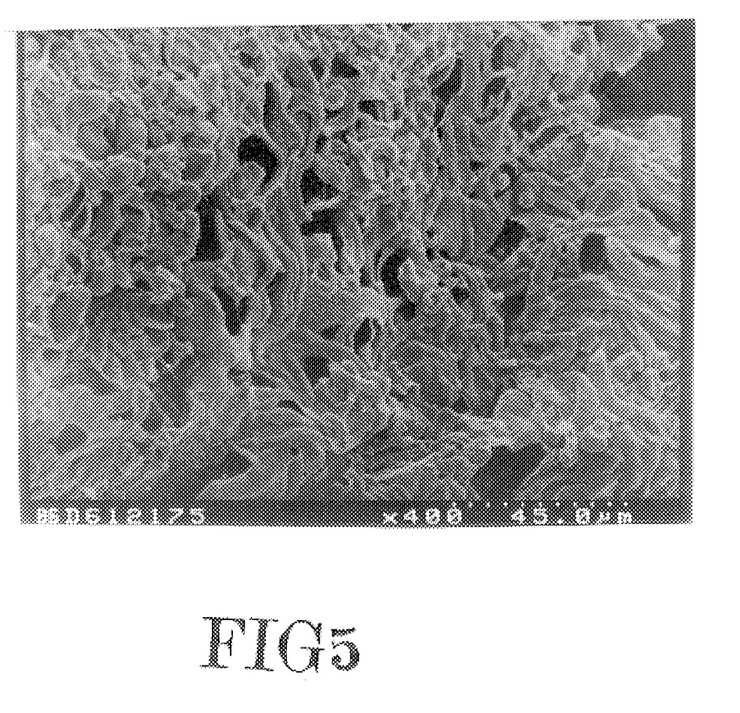
FIG. 5 is an electromicroscopic photograph (1440×) of natural collagen template after lyophilization.

In a comparison among the magnifications of the structures of the collagen templates, those reconstituted collagen templates cross-linked in the presence of 0.5%, 2.0% and 25% glutaraldehyde (FIGS. 1 to 3 respectively) are each in a net form with a regular pore size. Both of the structure and the pore size of the reconstituted collagen template cross-linked in the absence of glutaraldehyde (FIG. 4) were irregular. The natural collagen template (FIG. 5) was fibrous with irregular pores.

2.2.2. Evaluation of the Ultrastructure

The pore sizes and forms corresponding to the treatments of the reconstituted or natural collagen templates are listed in the following table.

| Treatments [cross-linked with glutaraldehyde % for day(s)] | Form of template | pore size (microns) |
|---|---|---|
| 0.5% for 11 days | net | 90–150 |
| 2.0% for 1 day | net | 50–80 |
| 25% for 1 day | net | 30–80 |
| 0% | irregular | irregular |
| natural | fibrous | irregular |

3. Animal Test 3.1. Animals

Forty-eight adult New Zealand male rabbits (average weight of 2.0 kg) were housed in well ventilated cages and fed with a regular diet (Purina Rabbit Chow, Purina Mills, Inc. Mo.). These animals were divided into "Gross" (6 animals) and "Histology" groups (42 animals). The six animals of the "Gross" group included 2 rabbits for 3 months observation after partial diskectomy with implantation, 2 rabbits for 3 months after partial diskectomy without implantation (negative control) and the remaining 2 for the sham-operation (blank control). The "Histology" group comprised 42 rabbits, consisting of 12 animals for observation 3 months, 1 animal for 2 months, 5 animals for 1 month and 1 animal for 1 week after partial diskectomy with implantation; and 7 animals for 3 months, 5 animals for 2 months, 9 animals for 1 month and 1 animal for 1 week after partial diskectomy without implantation. One animal for 5 months after partial diskectomy with implantation followed by 2 weeks after partial diskectomy without implantation. A non-operated side of each of the recipient animals served as an internal control. The "Gross" group was designated for identification of changes of the TMJ with or without implantation after partial diskectomy and the "Histology" group was designated for further histological identifications.

3.2. Surgical Operation

The TMJ region of each animal was shaved and prepared with povidone-iodine solution under a general anesthesia with Ketamine (35 mg/kg) and Citosol (50 mg/kg) and followed by lidocaine infiltration. Half of the TM joints were operated was on the right side and the other half were operated on the left side. The non-operated side was served as the internal control.

A curvilinear incision was made along a zygomatic arch extending from the lateral aspect of the canthus to intermediately anterior to the external auditory meatus. Overlying tissue was flapped interiorly to expose the TMJ. Following an incision along the articular fossa and the eminence, a 0.5 cm segment of zygomatic process was removed.

A partial diskectomy (3.5×2.0 mm$^2$) was made on the posterio-lateral portion of the TMJ disc. The reconstituted collagen templates (cross-linked with 2% glutaraldehyde for 24 hours) according to the present invention shaped as disks each with the thickness of 1.5 mm and the diameter of 5 mm were immediately implanted to the remaining of the disc and fixed. The articular capsule was closed with 4–0 silk non-resorbable suture.

3.3. Post-Surgical Preparation

After surgery, body weights of individual rabbits were measured weekly to determine whether problems of the operated TMJ were reflected in food intake. The animals were sacrificed after 1 week to 5.5 months by intraperitoneal injection of pentobarbital in a lethal dosage (60 mg/kg). The TMJ tissue with the implant was coronally excised and processed for gross and histological evaluation.

The TMJ tissue with implant was fixed in formalin, embedded in paraffin and serially sectioned (Sacura Sledge microtome) in thickness of 5 to 10 microns. The specimens were stained with hematoxylin/eosin.

Figure 6:
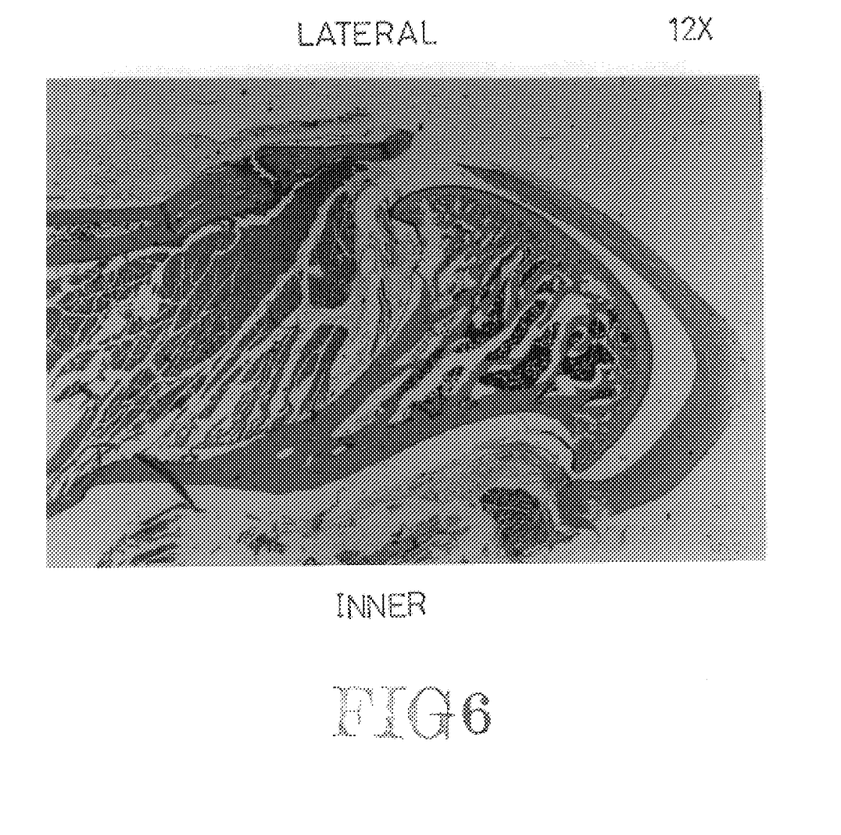
FIG. 6 is a photomicroscopic photograph (12×) of a coronal tissue section of the normal temporomandibular joint (TMJ) disc of a New Zealand rabbit.

3.4. Results:

(I) In the groups of sham-operated or non-operated animals, the meniscus disc and the articular surface are smooth, white and glistening. The histological examination also indicated the normal tissues, as shown in FIG. 6.

(II) Overview comments on the group only undergoing the partial diskectomy:

a. Ingrowth of the granulation tissues in the partially diskectomized region was observed in the second week after surgery.

b. Fibrosis was observed in the fourth week after the surgery.

c. Ossification and calcification were observed from 4 to 12 weeks after surgery.

Figure 7:
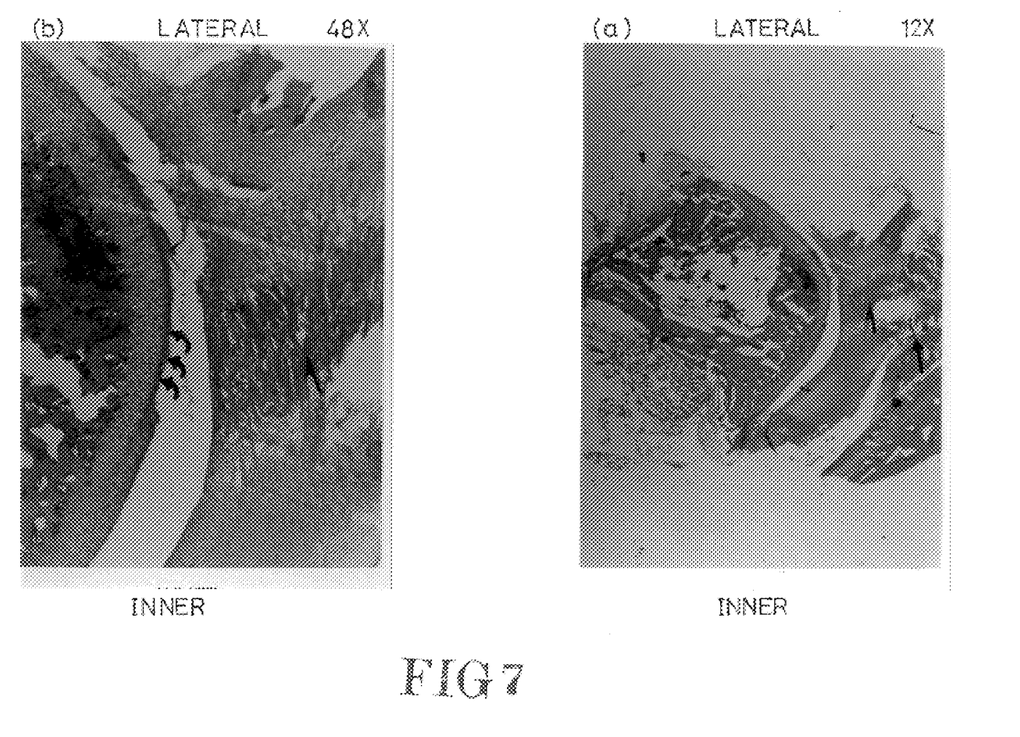

As shown in FIG. 7, the fibrosis (semi-arrow), the ossification occurring in the connection between the meniscus disc and epiphyses of temoporalmendibular bone (full-arrow) and the erosion of the articular cartilage (curve-arrow) are observed.

(III) Overview comments on the group undergoing the partial diskectomy and the subsequent implantation:

a. Ingrowth of the synovial cells in the partially diskectomized region was observed at the end of the first week after surgery.

b. Ingrowth of the fibrous chondrocytes in the partially diskectomized region was observed by the end of the 4th week after surgery.

c. Formation of dense collagen bundles in the partially diskectomized region was observed from 8 to 12 weeks after surgery.

d. The implants were not rejected and the infiltration of lymphocytes was not observed.

Figure 8:
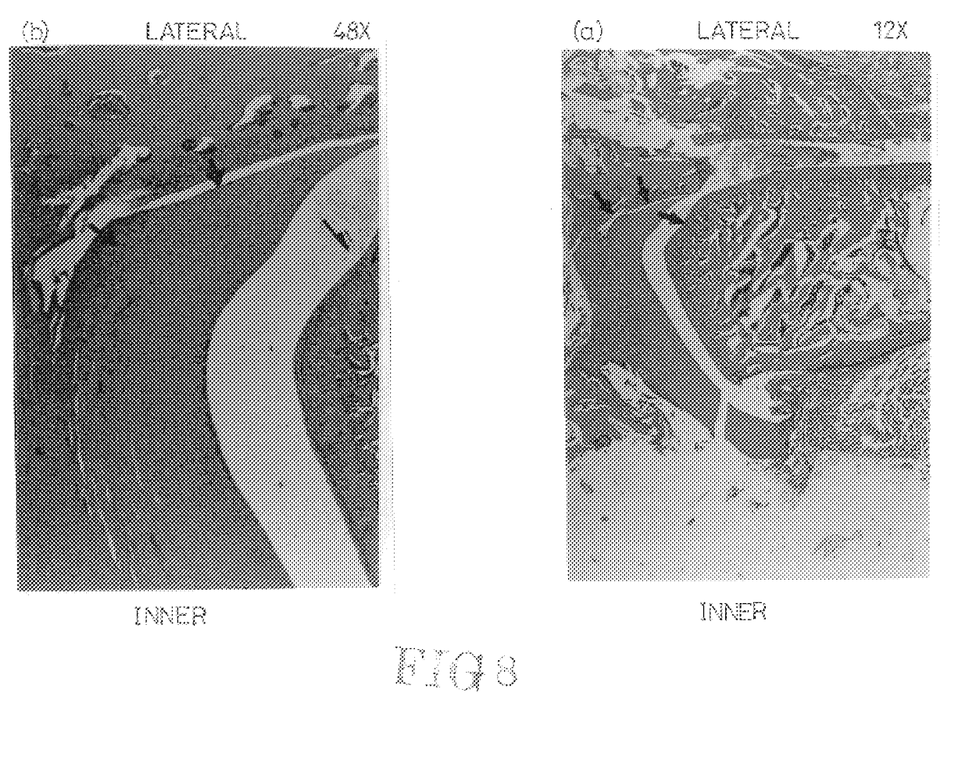

As shown in FIG. 8, the regeneration of the articular tissues (full-arrow) and a lower resorption on the surface of the epiphyses (semi-arrow) are observed. There is no erosion of the cartilage.

Figure 9:
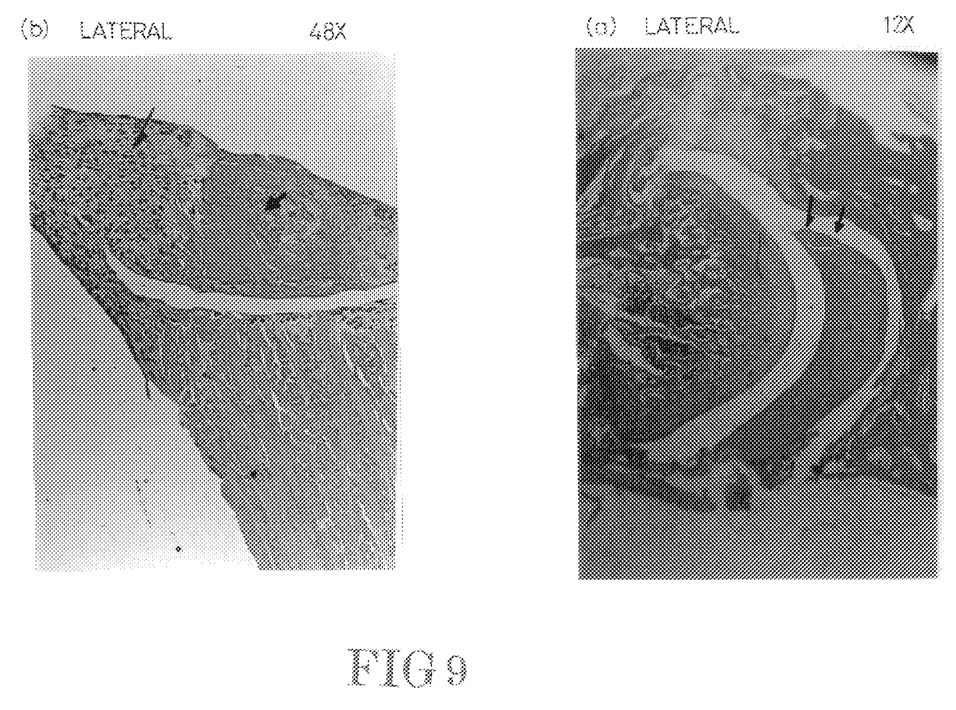
Figure 11:
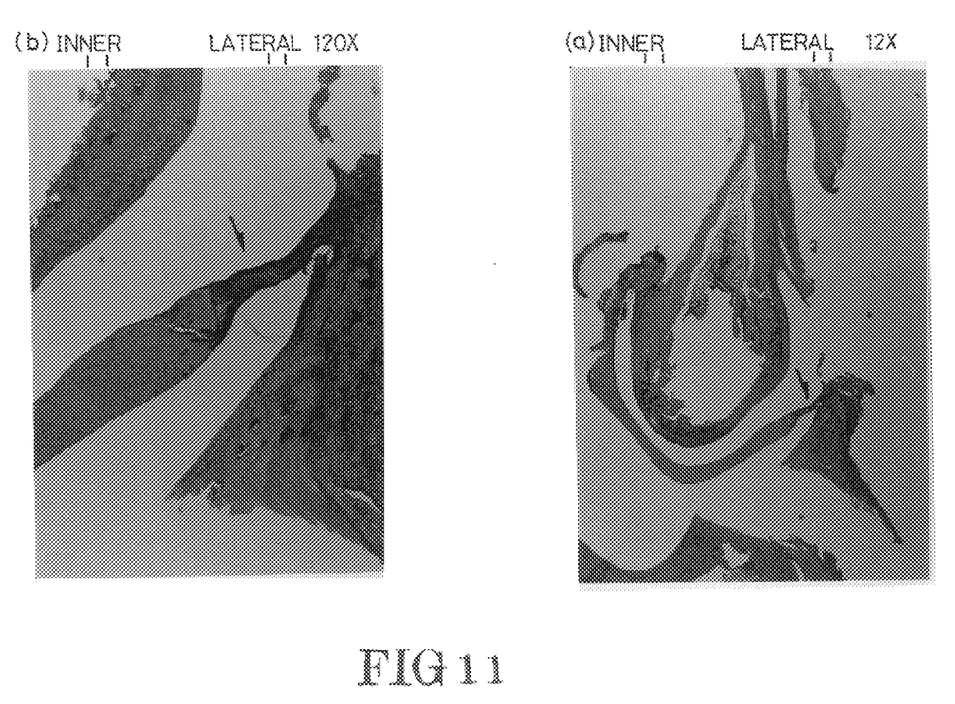

As shown in FIGS. 9 and 11, regeneration of the synovial cells (semi-arrow) and the chondrocytes (full-arrow) are observed.

Figure 10:
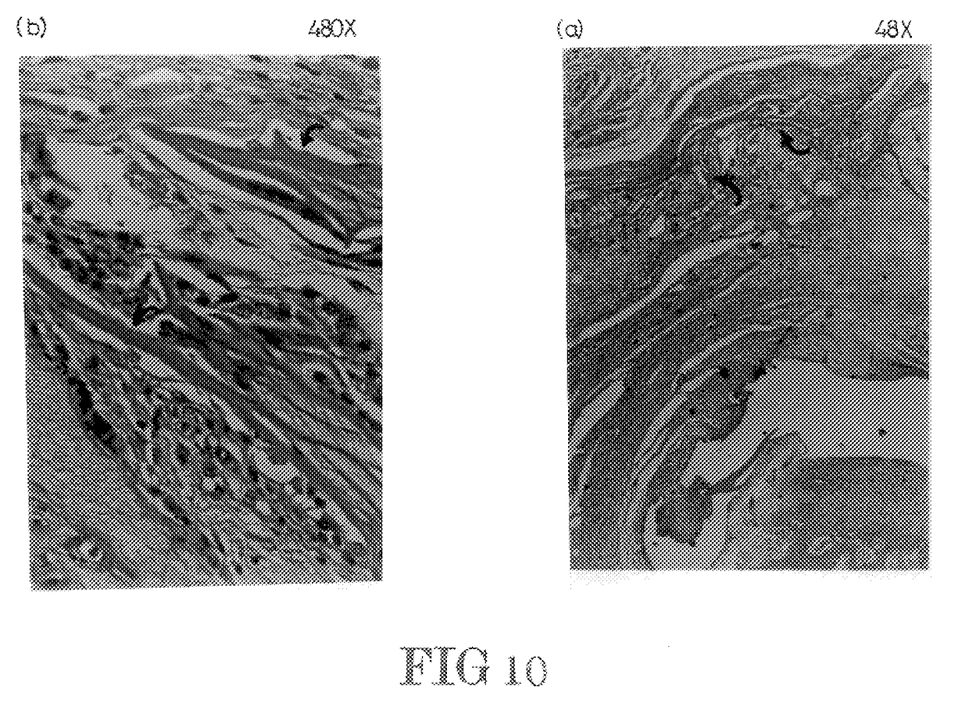

As shown in FIG. 10, residues of the implanted reconstituted collagen template according to the present invention are still visible (curve-arrow).

Figure 12:
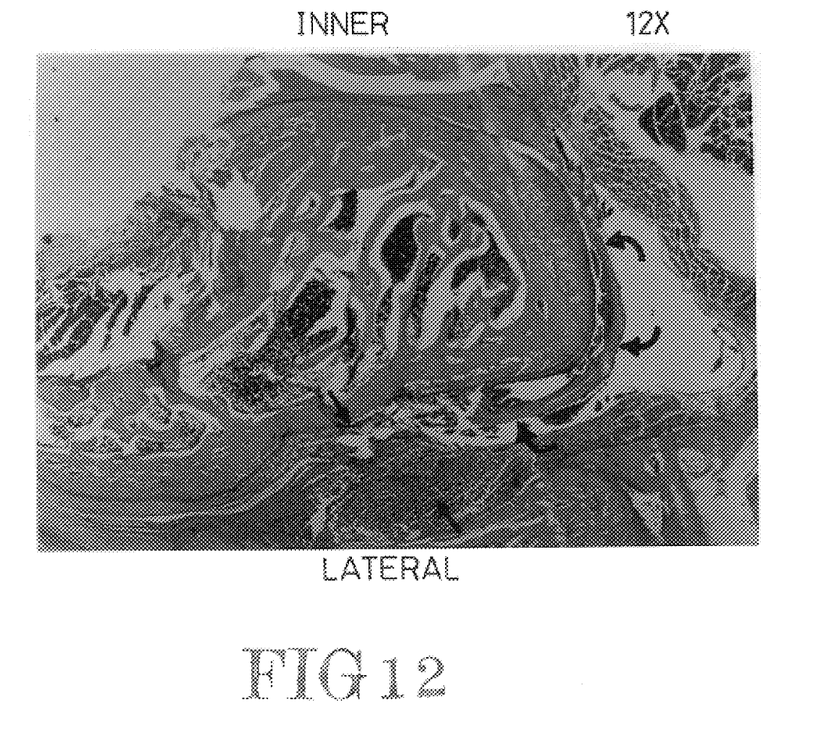
FIG. 12 is a photomicroscopic photograph (12×) of the coronal tissue section of the TMJ disc of the New Zealand rabbit undergoing a first partial diskectomy on the posterio-lateral portion and the implantation of the reconstituted collagen template according to the present invention and after 5 months undergoing a second partial diskectomy on the posterio-lateral portion without implantation for two weeks.

As shown in FIG. 12, recovery of the portion receiving the first diskectomy is observed (curve-arrow), on the contrary, inflammation and formation of the granulation tissues in the portion receiving the second diskectomy are observed (arrow).

4. Conclusion:

The reconstituted collagen templates according to the present invention could rebuild the TMJ disc by implantation in rabbits which have suffered from arthritis caused by the artificial partial diskectomy. According to the overviews of the gross and histological observations, it is believed that the reconstituted collagen template according to the present invention is able to activate the regeneration of the articular tissues and thereby cure the articular destruction.

Although the invention has been explained in relation to its preferred embodiment, it is to be understood that many other possible modifications and variations can be made without departing from the spirit and scope of the invention as hereinafter claimed.

I claim:

1. A process to prepare a reconstituted collagen template for regeneration of articular tissue, comprising:

(a) a starting solution of collagen in an aqueous solvent is heated at about 55° C. to 60° C. and acidified in a pH range of about 1.8 to 2.2 whereby an acid-insoluble fraction is obtained, and the acid-insoluble fraction is treated with pepsin in a ratio range of 1:5 to 1:10 (activity unit:mg collagen);

(b) a resultant collagen solution of (a) is reduced;

(c) a resultant collagen solution of (b) is treated with glutaraldehyde in an effective amount to generate a reconstituted collagen; and (d) the resultant reconstituted collagen of (c) is molded and lyophilized.

2. The process according to claim 1, wherein the collagen solution in (c) is treated with glutaraldehyde in an amount from 0.5 to 25% (v/v).

3. The process according to claim 1, wherein the reconstituted collagen is molded and lyophilized for 18 to 24 hours.

4. A reconstituted collagen template for use in activating regeneration of articular tissues and curing articular destruction in a mammal, which is a net form with a pore size of 30 to 150 microns.

5. The reconstituted collagen template according to claim 4, wherein the mammal is a human.

6. The process according to claim 2, wherein the collagen solution in (c) is treated with glutaraldehyde for 24 hours to 11 days.

* * * * *